US010745612B2

United States Patent
Recio, III et al.

(10) Patent No.: US 10,745,612 B2
(45) Date of Patent: Aug. 18, 2020

(54) SULFONATED IMINODIALKANOIC ACIDS FORMED FROM AN IMINODIALKYLNITRILE AND A SULTONE AND METHODS FOR USE THEREOF

(71) Applicant: Halliburton Energy Services, Inc., Houston, TX (US)

(72) Inventors: Antonio Recio, III, Humble, TX (US); Enrique Antonio Reyes, Tomball, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 16/099,148

(22) PCT Filed: Jun. 30, 2016

(86) PCT No.: PCT/US2016/040441
§ 371 (c)(1),
(2) Date: Nov. 5, 2018

(87) PCT Pub. No.: WO2018/004606
PCT Pub. Date: Jan. 4, 2018

(65) Prior Publication Data
US 2019/0211256 A1     Jul. 11, 2019

(51) Int. Cl.
*C09K 8/72*     (2006.01)
*C07C 303/02*     (2006.01)
(Continued)

(52) U.S. Cl.
CPC .............. *C09K 8/72* (2013.01); *C07C 303/02* (2013.01); *C07C 303/22* (2013.01); *C09K 8/52* (2013.01); *E21B 43/26* (2013.01)

(58) Field of Classification Search
CPC . C09K 8/52; C09K 8/72; C09K 8/035; C09K 8/04; E21B 43/26
See application file for complete search history.

(56) References Cited

U.S. PATENT DOCUMENTS

| | | |
|---|---|---|
| 2011/0257431 A1 | 10/2011 | Baumann et al. |
| 2012/0264973 A1 | 10/2012 | Baumann et al. |
| 2012/0302783 A1 | 11/2012 | Baumann et al. |

FOREIGN PATENT DOCUMENTS

| | | |
|---|---|---|
| CN | 103752601 | 4/2014 |
| JP | 10158226 | 6/1998 |

(Continued)

OTHER PUBLICATIONS

"Complexation of uranyl ions by N-(sulfoethyl)-iminodiacetic acid: hydrothermal synthesis, luminescence, and uranyl sequestration" by Yubo Shu et al. dated Dec. 8, 2014.

(Continued)

*Primary Examiner* — Zakiya W Bates
(74) *Attorney, Agent, or Firm* — Thomas Rooney; C. Tumey Law Group PLLC

(57) ABSTRACT

Complexation of metal ions using chelating agents within a subterranean formation can often be desirable, such as to temper the formation of metal-containing precipitates. However, many chelating agents are produced commercially in an alkali metal salt form that may not be entirely suitable for use downhole, particularly in subterranean formations containing a siliceous material. The working pH range of some types of chelating agents may also be limiting. Treatment fluids comprising an aqueous carrier fluid having an acidic pH, a sulfonated iminodialkanoic acid, and ammonium ions may at least partially address downhole precipitation issues, while providing further advantages as well. Methods for forming sulfonated iminodialkanoic acids can comprise reacting an iminodialkylnitrile with a sultone under acidic conditions to form a fluid comprising a sulfonated iminodialkanoic acid and ammonium ions.

5 Claims, 3 Drawing Sheets

(51) Int. Cl.
    *C09K 8/52*     (2006.01)
    *C07C 303/22*   (2006.01)
    *E21B 43/26*    (2006.01)

(56) References Cited

FOREIGN PATENT DOCUMENTS

| | | |
|---|---|---|
| JP | 2002356464 | 12/2002 |
| JP | 2010082600 | 4/2010 |
| SU | 802273 | 2/1981 |
| WO | 2009024518 | 2/2009 |
| WO | 2009024519 | 2/2009 |
| WO | 2009127982 | 10/2009 |
| WO | 2011151517 | 12/2011 |
| WO | 2016060685 | 4/2016 |

OTHER PUBLICATIONS

International Search Report and Written Opinion for Application No. PCT/US2016/040441 dated Jul. 31, 2017.

SULFONATED IMINODIALKANOIC ACIDS FORMED FROM AN IMINODIALKYLNITRILE AND A SULTONE AND METHODS FOR USE THEREOF

BACKGROUND

The present disclosure generally relates to complexation of metal ions and, more specifically, to dissolution of minerals, chelating agents suitable for use in conjunction with various subterranean treatment operations, and methods for synthesizing such chelating agents.

Treatment fluids can be used in a variety of subterranean treatment operations. Such treatment operations can include, without limitation, drilling operations, stimulation operations, production operations, remediation operations, sand control treatments, and the like. As used herein, the terms "treat," "treatment," "treating," and grammatical equivalents thereof refer to any subterranean operation that uses a fluid in conjunction with achieving a desired function and/or for a desired purpose. Use of these terms does not imply any particular action by the treatment fluid or a component thereof, unless otherwise specified herein. More specific examples of illustrative treatment operations can include, for example, drilling operations, fracturing operations, gravel packing operations, acidizing operations, scale dissolution and removal operations, sand control operations, consolidation operations, and the like.

Acidic treatment fluids are frequently utilized in the course of conducting various subterranean treatment operations. Illustrative uses of acidic treatment fluids during subterranean treatment operations include, for example, matrix acidizing of siliceous and/or non-siliceous formations, scale dissolution and removal processes, gel breaking, acid fracturing, and the like.

Acidizing operations may be performed to stimulate a subterranean formation and increase production of a hydrocarbon resource therefrom. During an acidizing operation, an acid-reactive material in the subterranean formation can be at least partially dissolved by one or more acids to expand existing flow pathways in the subterranean formation, to create new flow pathways in the subterranean formation, and/or to remove acid-soluble scale in the subterranean formation. Acidizing a subterranean formation's matrix can be particularly effective for stimulating production.

The material being reacted with an acidizing fluid can significantly dictate how an acidizing operation is performed. When acidizing a non-siliceous substance, such as a carbonate material, mineral acids, such as hydrochloric acid, may often be sufficient to affect dissolution. Organic acids may be used in a similar manner to hydrochloric acid when dissolving a non-siliceous substance, especially at temperatures exceeding about 180° C. Siliceous materials, in contrast, are only readily dissolvable using hydrofluoric acid, optionally in combination with other acids to maintain a low pH environment. As used herein, the term "siliceous" refers to a substance having the characteristics of silica, including silicates and/or aluminosilicates. Illustrative siliceous materials can include, for example, silica, silicates, aluminosilicates, and any combination thereof, optionally in further combination with a non-siliceous substance, such as a carbonate material. Most sandstone formations, for example, contain about 40% to about 98% sand quartz particles (i.e., silica), bonded together by various amounts of cementing materials, which may be siliceous in nature (e.g., aluminosilicates or other silicates) or non-siliceous in nature (e.g., carbonates, such as calcite).

Carbonate formations contain minerals that comprise a carbonate anion. Calcite (calcium carbonate), dolomite (calcium magnesium carbonate), and siderite (iron carbonate) represent illustrative examples. When acidizing a carbonate formation, acidity of the treatment fluid alone can often be sufficient to solubilize the carbonate material by converting the carbonate anion into carbon dioxide and leaching a metal ion into the treatment fluid. As the concentration of dissolved metal ions rises, particularly at higher pH values upon spending of the acid, the solubility limit of the metal ions may be exceeded and precipitation of scale may occur.

Siliceous formations can include minerals such as, for example, zeolites, clays and feldspars. As indicated above, siliceous formations are usually acidized with hydrofluoric acid, optionally in combination with another acid, in order to react the siliceous minerals and affect their dissolution. Dissolved silicon species can be particularly prone toward undergoing secondary reactions with alkali metal ions to form highly damaging alkali metal silicate precipitates. Co-present non-siliceous minerals, such as carbonate minerals, may be concurrently dissolved while acidizing a siliceous material and lead to further precipitation issues.

Calcium ions and other alkaline earth metal ions can be particularly problematic when acidizing either siliceous or non-siliceous formations. As indicated above, the solubility limit of the metal ions may be quickly exceeded and deposition of scale may occur upon spending of an acid. In the case of siliceous formations acidized with hydrofluoric acid, calcium ions liberated from a co-present carbonate material can react readily with free fluoride ions to form highly insoluble calcium fluoride. Other metal ions can prove similarly problematic in this regard, either by forming an insoluble reaction product with hydrofluoric acid or by themselves upon forming an insoluble material under the particular conditions present in a wellbore. Calcium fluoride and other types of scale formed from metal ions can be highly damaging to subterranean formations, possibly even more so than if the initial acidizing operation had not been performed in the first place.

One approach that has been used to address the issues associated with dissolved metal ions is to employ chelating agents, which can sequester the metal ions in a more soluble and less reactive form of a metal-ligand complex. As used herein, the terms "complex," "complexing," "complexation" and other variants thereof refer to the formation of a metal-ligand bond without reference to the mode of bonding. Although complexation of metal ions may involve a chelation process, complexation is not deemed to be limited in this manner. Once bound in a metal-ligand complex, the metal ions may have a significantly decreased propensity to undergo a further reaction to form scale.

There are difficulties associated with chelation strategies, however. At low pH values, the carboxylic acid groups of many chelating agents may be substantially protonated, a form that can be ineffective for promoting metal ion complexation. This issue can significantly limit the working pH range over which an acidizing operation may take place, potentially limiting the acidizing operation's speed and effectiveness (i.e., by working at higher pH values). In addition, many chelating agents are commercially supplied in their alkali metal salt forms, which can be especially problematic for siliceous formations due to the precipitation issues noted above. Conversion of the alkali metal salt form of a chelating agent into the free acid form or an alternative salt form can often be problematic and/or expensive, particularly at the large scales needed to support subterranean treatment operations. Although numerous chelating agents are known, there are presently a very limited number available in suitable form and in sufficient supply to support widespread downhole use. Provisions for working with the less desirable alkali metal salt forms of commodity chelating agents presently may need to be made in order to facilitate their use in subterranean treatment operations.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, as will occur to one having ordinary skill in the art and the benefit of this disclosure.

DETAILED DESCRIPTION

Figure 1:
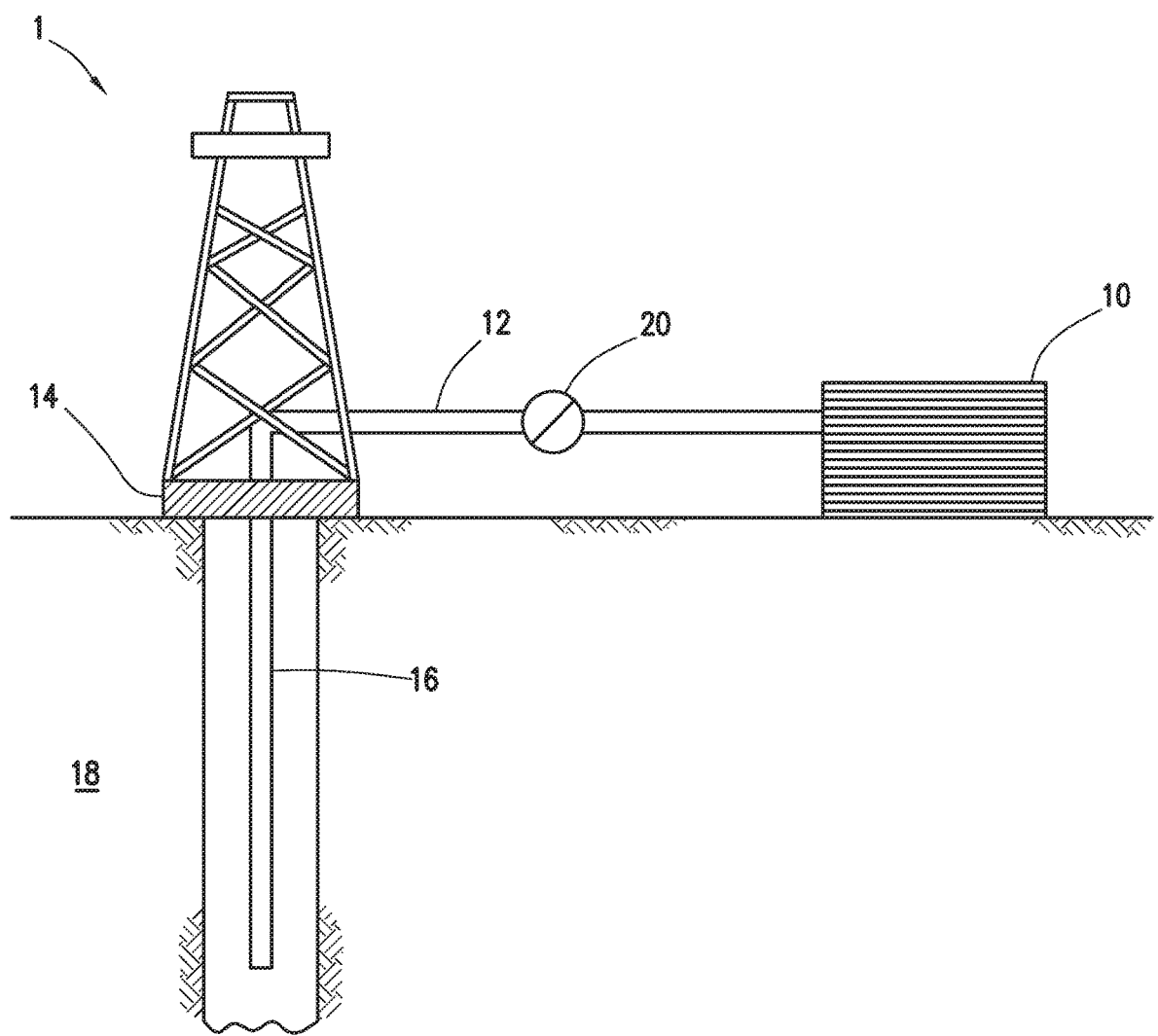
FIG. 1 shows an illustrative schematic of a system that can deliver treatment fluids of the present disclosure to a downhole location, according to one or more embodiments.

The present disclosure generally relates to complexation of metal ions and, more specifically, to dissolution of minerals, chelating agents suitable for use in conjunction with various subterranean treatment operations, and methods for synthesizing such chelating agents.

One or more illustrative embodiments incorporating the features of the present disclosure are presented herein. Not all features of a physical implementation are necessarily described or shown in this application for the sake of clarity. It is to be understood that in the development of a physical implementation incorporating the embodiments of the present disclosure, numerous implementation-specific decisions may be made to achieve the developer's goals, such as compliance with system-related, business-related, government-related and other constraints, which may vary by implementation and from time to time. While a developer's efforts might be time-consuming, such efforts would be, nevertheless, a routine undertaking for one having ordinary skill in the art and the benefit of this disclosure.

As discussed above, there are various issues associated with the use of chelating agents in subterranean acidizing operations. In some instances, the working pH range of the acidizing operation may be limited in order to maintain the chelating agent in an active form. Moreover, the as-supplied alkali metal salt form of many chelating agents can be extremely problematic, particularly when used in conjunction with acidizing a subterranean formation containing a siliceous material. These issues frequently occur with aminopolycarboxylic acid chelating agents, which can otherwise be desirable for use in subterranean treatment operations due to their ready complexation properties and environmentally friendly character in many cases. Although the salt form of a chelating agent may be changed through acidification and ion exchange, these processes may be labor intensive, expensive and incompatible with commercial-scale production. Moreover, unless liberated alkali metal ions are removed from a solution of the chelating agent, they can still end up in a formulated treatment fluid and lead to the deleterious consequences noted above.

The present inventors discovered a new type of chelating agent that overcomes several of the above issues and provides related advantages as well. Namely, the inventors discovered that sulfonated aminopolycarboxylic acids, more specifically sulfonated iminodialkanoic acids such as sulfonated iminodiacetic acids, can be especially advantageous for use in acidizing operations. As used herein, the term "sulfonated" refers to the condition of a compound bearing a sulfonic acid group. Due to the presence of the very acidic sulfonic acid group, sulfonated iminodialkanoic acids can maintain high solubility levels and low pH values in aqueous fluids, such as in aqueous acidizing fluids.

The inventors discovered various synthetic approaches through which sulfonated iminodialkanoic acids may be readily obtained in a form that is substantially free of alkali metal ions. Depending upon the chosen synthetic approach, the free acid form or an ammonium salt form of the sulfonated iminodialkanoic acids may be obtained. Such synthetic approaches desirably avoid the use of base-promoted alkylation reactions that might otherwise introduce unwanted alkali metal ions into these types of compounds.

In one synthetic approach, the inventors discovered that sulfonated iminodialkanoic acids may be synthesized in their free acid form under acidic conditions via a ring-opening process without alkali metal ions being present. Specifically, an iminodialkanoic acid (e.g., iminodiacetic acid) may be reacted in high yields with a sultone (e.g., 1,2-oxathietane 2,2-dioxide-ethane sultone, 1,2-oxathiolane 2,2-dioxide-1,3-propane sultone, 1,2-oxathiane 2,2-dioxide-1,4-butane sultone, or various derivatives thereof) under acidic conditions to accomplish the foregoing. The foregoing sultones are commercially available and can directly produce the free acid form of the sulfonated iminodialkanoic acid in a fluid concentrate that is substantially free of alkali metal ions. The fluid concentrate may then be employed directly as a treatment fluid or undergo further dilution with a carrier fluid and/or other substances of interest to form a treatment fluid that is substantially free of alkali metal ions. Sulfonated iminodialkanoic acids that are substantially free of alkali metal ions may be particularly advantageous for acidizing a siliceous formation for the reasons discussed above.

In an improvement of the above-described ring-opening process, the inventors discovered that an iminodialkylnitrile can be substituted for an iminodialkanoic acid and undergo a reaction under similar conditions to yield the same types of sulfonated iminodialkanoic acids. Under the acidic reaction conditions under which ring-opening occurs, the nitrile groups also undergo hydrolysis in situ to form carboxylic acid functionalities. Unlike syntheses proceeding directly from an iminodialkanoic acid, utilizing an iminodialkylnitrile as an acid precursor allows ammonium ions to be produced in conjunction with the sulfonated iminodialkanoic acid. Ammonium ions can be a particularly desirable ionic form for use in conjunction with acidizing operations, such as to provide clay stabilization effects, not to mention avoiding the above-described formation of insoluble fluorine-containing compounds derived from alkali metal ions. The ability to form ammonium ions in situ can obviate the need to modify a treatment fluid further to introduce ammonium ions thereto. Iminodialkanoic acids and their corresponding iminodialkylnitriles can also be fairly comparable in terms of price, so the alternative synthetic approach providing in situ ammonium ion formation does not add significantly to cost burdens for forming a treatment fluid.

Regardless of how they are synthesized, sulfonated iminodialkanoic acids can be particularly advantageous in acidizing operations, since they can bear sufficient acidity alone to dissolve an acid-reactive substance, such as a carbonate material, without another acid being present to decrease the pH. All of the acidic groups in sulfonated iminodialkanoic acids have pKa values under 6, with the most acidic group reaching negative $pK_a$ values, which can allow each acidic group to contribute to at least some degree in acid-promoted dissolution processes. Accordingly, due to their strong acidity, sulfonated iminodialkanoic acids can, in some instances, serve as a direct replacement for mineral acids and organic acids that are commonly used in acidizing operations. Optionally, a mineral acid or an organic acid can be used in combination with a sulfonated iminodialkanoic acid to further promote dissolution of an acid-reactive substance. In particular embodiments, when used in conjunction with acidizing a subterranean formation containing a siliceous material, hydrofluoric acid or a hydrofluoric acid-generating compound can be used in combination with the sulfonated iminodialkanoic acids described herein. Alkali metal ions can be excluded from the treatment fluids in either case, thereby allowing the advantages herein to be realized.

Due to their ability to serve as an effective direct replacement for a mineral acid or an organic acid, sulfonated iminodialkanoic acids may also be used as a secondary acid source in combination with another chelating agent. When combined with one or more other chelating agents, the sulfonated iminodialkanoic acid and the other chelating agents may promote complexation of different metal ions and/or provide effectiveness over differing pH ranges. For example, the sulfonated iminodialkanoic acid may complex metal ions at low pH values, and the other chelating agent(s) may promote complexation at higher pH values.

In spite of their strong acidity, sulfonated iminodialkanoic acids can advantageously remain active for promoting metal ion complexation and lessen the likelihood of precipitate occurrence during subterranean treatment operations. In particular, sulfonated iminodialkanoic acids can maintain a high affinity for promoting complexation of calcium ions, other alkaline earth metal ions, and transition metal ions. Accordingly, sulfonated iminodialkanoic acids of the present disclosure can promote dissolution of metal-containing substances through both their acidity and their complexation properties.

Further, the sulfonated iminodialkanoic acids described herein may be readily utilized in acidizing operations conducted in a carbonate formation or in a siliceous formation without significantly modifying the chelating agent's composition in a treatment fluid. In the case of acidizing a siliceous formation, hydrofluoric acid or a hydrofluoric acid-generating compound can be present in a treatment fluid containing the sulfonated iminodialkanoic acid or be introduced separately to a subterranean formation to promote dissolution of a siliceous material therein. As described above, ammonium ions in treatment fluids formed through in situ nitrile hydrolysis can be especially advantageous, particularly when clays and other siliceous materials are present and undergoing dissolution. The ability to use the sulfonated iminodialkanoic acids described herein in both types of acidizing operations may significantly simplify these oilfield operations and decrease their costs. As a further advantage, the sulfonated iminodialkanoic acids described herein may possess anti-scaling properties, which can also be beneficial for conducting a treatment operation.

In various embodiments, the sulfonated iminodialkanoic acids described herein may have the structure shown in Formula 1

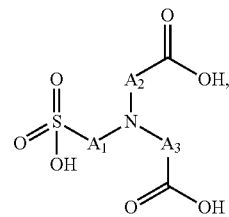

Formula 1 wherein $A_1$ is a C1-C4 alkyl group, which may be substituted or unsubstituted and contain optional branching, and $A_2$ and $A_3$ are independently C1-C10 alkyl groups, which may be the same or different and may be substituted or unsubstituted and contain optional branching. In more particular embodiments, the sulfonated iminodialkanoic acids described herein may have the structure shown in Formula 2

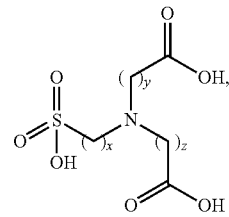

Formula 2 wherein x is an integer ranging between 1 and 4, and y and z are independently integers ranging between 1 and about 10, or between 1 and about 3. In still more particular embodiments, the sulfonated iminodialkanoic acids described herein can be sulfonated iminodiacetic acids having the structure shown in Formula 3

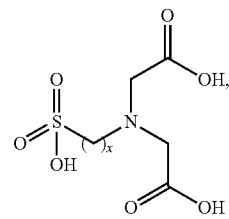

Formula 3 in which x is defined as above. Sulfonated iminodiacetic acids in which x is 3 can be formed readily from 1,3-propane sultone.

As indicated above, various synthetic approaches can be used to form the sulfonated iminodialkanoic acids of the present disclosure. Illustrative synthetic approaches are discussed in more detail hereinafter. In the description that follows, the synthesis of sulfonated iminodialkanoic acids will be exemplified through the synthesis of sulfonated iminodiacetic acids. It is to be recognized, however, that other sulfonated iminodialkanoic acids may be produced by utilizing a different iminodialkanoic acid starting material or a precursor thereof.

In some embodiments, iminodiacetic acid or a salt thereof may be alkylated under basic conditions with a haloalkyl-sulfonic acid or a salt thereof, as shown in Reaction 1, wherein X is a halide or a halide equivalent, such as an alkylsulfonate or an arylsulfonate, and x is defined as above.

Reaction 1

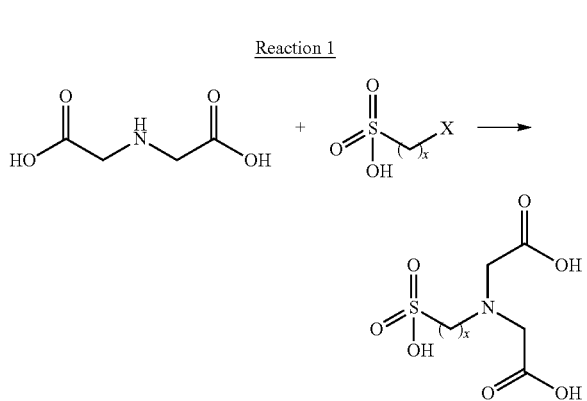

In some instances, alkali metal ions introduced from the base can be difficult to remove from the resulting sulfonated iminodiacetic acid. In the event that exclusion of alkali metal ions is desired, ammonium hydroxide or other bases may be used to promote the alkylation process. Competing elimination reactions occurring at high pH can also be problematic in this approach. Similar approaches starting from iminodiacetonitrile can also be used to produce sulfonated iminodiacetic acids, with nitrile hydrolysis taking place in situ under basic conditions or under acidic conditions in a separate reaction step. Again, the introduction of unwanted alkali metal ions can be problematic, and competing reactions can occur.

As indicated above, the inventors discovered alternative approaches for synthesizing sulfonated iminodiacetic acids in their free acid form by reacting iminodiacetic acid with a sultone under acidic conditions. Such approaches can proceed with the substantial exclusion of problematic alkali metal ions. The general approach utilizing iminodiacetic acid and a sultone to form a sulfonated iminodiacetic acid is exemplified in Reaction 2, wherein A is $(CH_2)_x$ and x is 2, 3 or 4.

Reaction 2

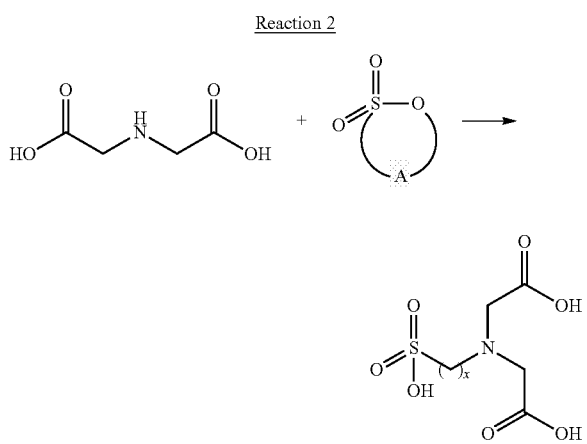

The particular example utilizing 1,3-propane sultone as the reaction partner for iminodiacetic acid is shown in Reaction 3.

Reaction 3

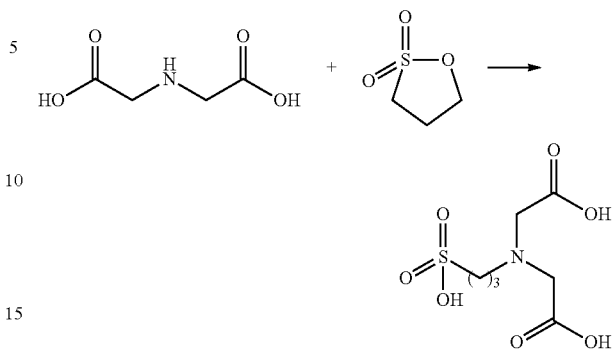

Similarly, Reaction 4 shows the advantageous synthetic approach of the present disclosure, whereby a sulfonated iminodiacetic acid can be produced in conjunction with ammonium ions (not shown) through reacting iminodiacetonitrile with a sultone under acidic conditions, wherein A is $(CH_2)_x$ and x is 2, 3 or 4.

Reaction 4

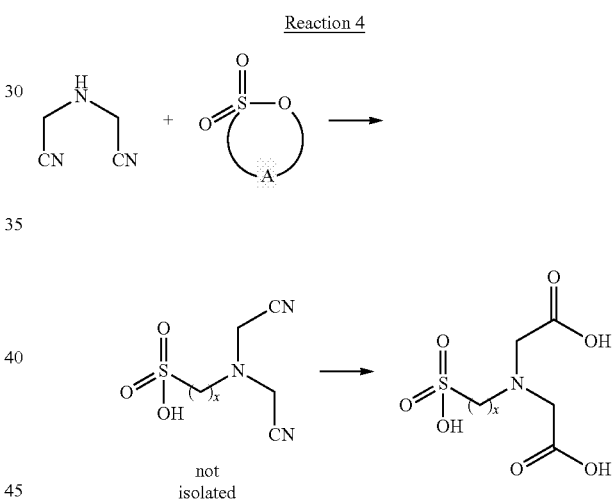

not isolated

Under the acidic reaction conditions, the initially produced sulfonated iminodiacetonitrile undergoes hydrolysis to the corresponding sulfonated iminodiacetic acid with the concurrent production of ammonium ions. Although the sulfonated iminodiacetonitrile intermediate could, in principle, be isolated, it can more desirably be hydrolyzed in situ such that the sulfonated iminodiacetic acid is formed in a single pot from the iminodiacetonitrile. The particular example utilizing 1,3-propane sultone as the reaction partner for iminodiacetonitrile is shown in Reaction 5.

Reaction 5

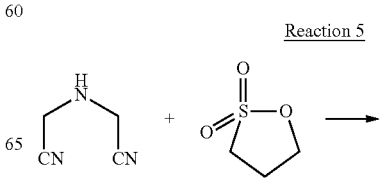

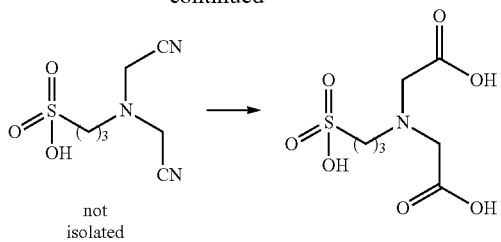

not isolated

In addition to the ability to form sulfonated iminodialkanoic acids in the absence of alkali metal ions, advantages of the synthetic approaches exemplified in Reactions 2-5 include the benefit that the sulfonated iminodiacetic acids form in near-quantitative yields as a concentrate in an aqueous reaction medium. The concentrate may be used directly in an acidizing operation or undergo dilution with a carrier fluid in the course of formulating an acidizing fluid. Accordingly, in some embodiments, treatment fluids of the present disclosure may be formulated or produced such that they are substantially free of alkali metal ions. As used herein, the term "substantially free of alkali metal ions" refers to an alkali metal content of about 5 wt. % or less, particularly an alkali metal content of about 1 wt. % or less.

Accordingly, in various embodiments, certain methods of the present disclosure can comprise reacting an iminodialkylnitrile with a sultone under acidic conditions to form a fluid comprising a sulfonated iminodialkanoic acid and ammonium ions. Such synthetic methods are exemplified by Reactions 4 and 5 above, and illustrative sulfonated iminodialkanoic acids of this type are shown in Formulas 1-3 above. In more particular embodiments, the iminodialkanoic acid can have a structure corresponding to Formula 3, in which x is an integer ranging between 1 and about 6, or 2, 3, or 4, in particular. Accordingly, in such embodiments, the methods can include reacting iminodiacetonitrile with a sultone that can be ethane sultone, 1,3-propane sultone, or 1,4-butane sultone.

In illustrative embodiments, the acidic conditions under which the iminodialkanoic acid is synthesized can comprise an aqueous solution having a pH of about 2 or less and containing the iminodialkylnitrile and the sultone. Any suitable acid can be used to produce the acidic conditions in the aqueous solution. Illustrative acids that can be suitable in this regard include mineral and organic acids such as, for example, hydrochloric acid, hydrobromic acid, hydrofluoric acid, formic acid, acetic acid, chloroacetic acid, dichloroacetic acid, trichloroacetic acid, methanesulfonic acid, citric acid, maleic acid, glycolic acid, lactic acid, malic acid, oxalic acid, the like, and any combination thereof. Hydrofluoric acid can be present when the treatment fluids are used to affect dissolution of siliceous materials, as discussed further herein.

In some embodiments, the iminoalkylnitrile can be reacted with the sultone under the acidic conditions at a temperature of about 80° C. or less. Lower reaction temperatures can help preclude unwanted expulsion of ammonia from the reaction mixture. In other illustrative embodiments, the reaction to form the sulfonated iminodialkanoic acid may occur at a temperature ranging between about 50° C. and about 100° C., or between about 60° C. and about 80° C.

In other various embodiments, certain methods for synthesizing a sulfonated iminodialkanoic acid can comprise reacting an iminodialkanoic acid with a sultone under acidic conditions to form a fluid comprising a sulfonated iminodialkanoic acid. Such synthesis methods are exemplified by Reactions 2 and 3 above, which are differentiated from Reactions 4 and 5 in that they do not produce ammonium ions in situ. Illustrative reaction conditions for forming sulfonated iminodialkanoic acids in this manner are similar to those provided above an iminodialkylnitrile as a starting material.

Accordingly, in some embodiments, the present disclosure provides treatment fluids comprising an aqueous carrier fluid having an acidic pH, a sulfonated iminodialkanoic acid, and ammonium ions. In some embodiments, the sulfonated iminodialkanoic acid can be in its fully protonated form. In other embodiments, the sulfonated iminodialkanoic acid can be at least partially deprotonated in the acidic aqueous solution, in which case the ammonium ions can serve as a counterion to provide charge balance. The presence of ammonium ions can be advantageous for the reasons discussed above.

Aqueous carrier fluids used for forming the treatment fluids of the present disclosure may be obtained from any suitable source. In some embodiments, suitable aqueous carrier fluids may include, for example, fresh water, acidified water, treated water, salt water, seawater, brackish water, produced water, flowback water, brine (e.g., a saturated salt solution), or an aqueous salt solution (e.g., a non-saturated salt solution). When it is desired for the treatment fluids to be substantially free of alkali metal ions, certain aqueous carrier fluids (e.g., salt water, seawater, brine, aqueous salt water, and the like) may not be suitable, unless they have undergone a treatment to remove a substantial portion of their alkali metal ions.

In further embodiments, an organic co-solvent may be present in the treatment fluids in combination with the aqueous carrier fluid. Suitable organic co-solvents may include, but are not limited to, glycols and alcohol solvents, for example. When present, an amount of the organic co-solvent may range between about 1% to about 50% by volume of the treatment fluid.

In various embodiments, the treatment fluid may have a pH of about 4 or less, or a pH of about 3 or less, or a pH of about 2 or less, or a pH of about 1 or less. If the pH of the concentrate or a combination of the concentrate and a carrier fluid is not in a desired range, the methods described herein may further comprise raising the pH of the treatment fluid with a base prior use of the treatment fluid in a subterranean formation. In some embodiments, ammonium hydroxide may comprise a suitable base for raising the pH, particularly if the treatment fluid is to be maintained in a form that is substantially free of alkali metal ions. Amine bases may also be suitable in this regard. Alkali metal bases may be suitable if there is no need to maintain the treatment fluids free of alkali metal ions. Acids or acid-generating compounds may be used similarly to lower the pH, if desired.

In some embodiments, the treatment fluids containing the sulfonated iminodialkanoic acid may further comprise an acid or an acid-generating compound. The acid or acid-generating compound may supplement the innate acidity of the sulfonated iminodialkanoic acid so that the treatment fluid spends less quickly. Both organic acids and mineral acids may be used for this purpose. Examples of organic and mineral acids that may be suitable in this regard include, for example, hydrochloric acid, hydrobromic acid, hydrofluoric acid, formic acid, acetic acid, chloroacetic acid, dichloroacetic acid, trichloroacetic acid, methanesulfonic acid, citric acid, maleic acid, glycolic acid, lactic acid, malic acid, oxalic acid, gluconic acid, succinic acid, tartaric acid, sulfamic acid, the like, and any combination thereof. It may be particularly desirable to include hydrofluoric acid in the treatment fluids when acidizing a subterranean formation comprising a siliceous mineral or a subterranean formation of mixed mineralogy comprising both a siliceous mineral and a carbonate mineral.

Suitable acid-generating compounds can include, for example, esters, aliphatic polyesters, orthoesters, poly(orthoesters), poly(lactides), poly(glycolides), poly(ε-caprolactones), poly(hydroxybutyrates), poly(anhydrides), ethylene glycol monoformate, ethylene glycol diformate, diethylene glycol diformate, glyceryl monoformate, glyceryl diformate, glyceryl triformate, triethylene glycol diformate, formate esters of pentaerythritol, the like, any derivative thereof, and any combination thereof.

In some embodiments, treatment fluids of the present disclosure may further comprise hydrofluoric acid or a hydrofluoric acid-generating compound. Suitable hydrofluoric acid-generating compounds may include substances such as, for example, fluoroboric acid, fluorosulfuric acid, hexafluorophosphoric acid, hexafluoroantimonic acid, difluorophosphoric acid, hexafluorosilicic acid, potassium hydrogen difluoride, sodium hydrogen difluoride, polyvinylammonium fluoride, polyvinylpyridinium fluoride, pyridinium fluoride, imidazolium fluoride, ammonium fluoride, tetrafluoroborate salts, hexafluoroantimonate salts, hexafluorophosphate salts, bifluoride salts (e.g., ammonium bifluoride), perfluorinated organic compounds, boron trifluoride and various boron trifluoride complexes.

When used, a hydrofluoric acid-generating compound can be present in the treatment fluids described herein in an amount ranging between about 0.1% to about 20% by weight of the treatment fluid. In other embodiments, an amount of the hydrofluoric acid-generating compound can range between about 0.5% to about 10% by weight of the treatment fluid or between about 0.5% to about 8% by weight of the treatment fluid. Hydrofluoric acid, when present, may be used in similar concentration ranges.

In further embodiments, the treatment fluids described herein may further comprise any number of additives that are commonly used in downhole operations including, for example, silica scale control additives, corrosion inhibitors, surfactants, gel stabilizers, anti-oxidants, polymer degradation prevention additives, relative permeability modifiers, scale inhibitors, foaming agents, defoaming agents, antifoaming agents, emulsifying agents, de-emulsifying agents, iron control agents, proppants or other particulates, particulate diverters, acids, fluid loss control additives, gas, catalysts, clay control agents, dispersants, flocculants, scavengers (e.g., $H_2S$ scavengers, $CO_2$ scavengers or $O_2$ scavengers), gelling agents, lubricants, friction reducers, bridging agents, viscosifiers, weighting agents, solubilizers, pH control agents (e.g., buffers), hydrate inhibitors, consolidating agents, bactericides, catalysts, clay stabilizers, breakers, delayed release breakers, and the like. Any combination of these additives may be used as well. One of ordinary skill in the art will be able to formulate a treatment fluid having properties suitable for a given application.

In other various embodiments, methods for treating a subterranean formation are described herein. In some embodiments, the methods may comprise: providing a treatment fluid comprising an aqueous carrier fluid having an acidic pH, a sulfonated iminodialkanoic acid, and ammonium ions; introducing the treatment fluid into a subterranean formation; and complexing one or more metal ions in the subterranean formation with the sulfonated iminodialkanoic acid. In additional embodiments, the methods may further comprise dissolving an acid-reactive substance in the subterranean formation with the treatment fluid to generate the one or more metal ions. In various embodiments, the acid-reactive substance may comprise a carbonate material or a siliceous material, as discussed further herein.

In further embodiments, providing the treatment fluid may comprise reacting an iminodialkylnitrile with a sultone under acidic conditions in an aqueous solution to form the sulfonated iminodialkanoic acid. In such embodiments, the treatment fluid can be substantially free of alkali metal ions and the ammonium ions can be formed in situ. The sulfonated iminodialkanoic acid may be formed in a concentrate having an acidic pH, which may be used directly as a treatment fluid in an acidizing operation or after undergoing additional dilution with a carrier fluid.

In alternative embodiments, providing the treatment fluid may comprise reacting an iminodialkanoic acid with a sultone under acidic conditions in an aqueous solution to form the sulfonated iminodialkanoic acid. In such embodiments, a source of ammonium ions, such as ammonium hydroxide or ammonium chloride, may be added to the aqueous solution after forming the sulfonated iminodialkanoic acid.

In more specific embodiments, providing the treatment fluid may comprise reacting iminodiacetonitrile with 1,3-propane sultone in an aqueous solution under acidic conditions to form a concentrate comprising a sulfonated iminodiacetic acid, and optionally, diluting the concentrate with a carrier fluid.

In some embodiments, the concentrate obtained from the reaction to form the sulfonated iminodialkanoic acid may be used directly in a treatment operation without further dilution. In such embodiments, a concentration of the sulfonated iminodialkanoic acid in the treatment fluid and in the concentrate may range between about 0.1 M to about 5 M. In more particular embodiments, the concentration may range between about 0.5 M and about 5 M, or between about 1 M and about 5 M, or between about 2 M and about 5 M, or between about 2 M and about 4 M. Dilution of the concentrate with a carrier fluid may be used to lower the concentration of the sulfonated iminodialkanoic acid to a suitable working range, which may include a range between about 0.01 M and about 4 M in some embodiments.

In other more specific embodiments, methods of the present disclosure may comprise: providing a treatment fluid comprising an aqueous carrier fluid having an acidic pH, a sulfonated iminodialkanoic acid, and ammonium ions; introducing the treatment fluid into a subterranean formation; at least partially dissolving an acid-reactive substance in the subterranean formation in the presence of the sulfonated iminodialkanoic acid to generate one or more metal ions; and complexing the one or more metal ions in the subterranean formation with the sulfonated iminodialkanoic acid.

In the methods of the present disclosure, a sulfonated iminodialkanoic acid may complex one or more metal ions in order to mitigate the metal ions' ability to undergo secondary reactions and form a precipitate within the subterranean formation. The resulting metal complexes may remain within the subterranean formation, or they may be produced therefrom before or concurrent with production of a hydrocarbon resource. In some embodiments, the metal complexes may remain soluble within the treatment fluid. In some embodiments, complexation of metal ions may, at least in part, promote dissolution of an acid-reactive substance by the sulfonated iminodialkanoic acids described herein.

In other embodiments, acidity of sulfonated iminodialkanoic acids may directly promote dissolution of an acid-reactive substance without complexation taking place. As indicated above, the sulfonated iminodialkanoic acids described herein are highly acidic substances by themselves, and in addition to their metal complexation properties, they may also promote dissolution of an acid-reactive substance containing metal ions through their acidity. Accordingly, in some embodiments, the sulfonated iminodialkanoic acid may be present alone in a treatment fluid, such that the treatment fluid is free of mineral acids and other organic acids. In some embodiments, the sulfonated iminodialkanoic acid may serve as a replacement for a mineral acid, such as hydrochloric acid, in a treatment fluid. This may particularly be the case when the treatment fluids of the present disclosure are used for acidizing a subterranean formation that primarily comprises a carbonate mineral such as calcite, dolomite, or the like.

In some embodiments, however, treatment fluids comprising a sulfonated iminodialkanoic acid and ammonium ions may further comprise an acid or an acid-generating compound. Suitable acids and acid-generating compounds that may be present are described above. The acid or acid-generating compound may supplement the innate acidity of the sulfonated iminodialkanoic acid so that the treatment fluid spends less quickly.

In more particular embodiments, the acid-reactive substance may comprise a carbonate mineral. Carbonate minerals that may undergo dissolution in the presence of the treatment fluids of the present disclosure include, for example, calcite (calcium carbonate), dolomite (calcium magnesium carbonate), siderite (iron carbonate), or any combination thereof. Particularly when acidizing a calcite or dolomite formation, the one or more metal ions that are complexed by the chelating agent may comprise at least calcium ions. When acidizing a subterranean formation comprising siderite, the one or more metal ions undergoing complexation by the chelating agent may comprise iron ions and iron control may be achieved. In either case, by complexing the metal ions with the sulfonated iminodialkanoic acid, the solubility limit of the metal ions may be increased relative to the uncomplexed form, thereby lessening the likelihood of damaging precipitates forming within the subterranean formation.

In more specific embodiments, metal ions that may be complexed by the sulfonated iminodialkanoic acid include alkaline earth metal ions, transition metal ions, main group metal ions, lanthanide ions, or any combination thereof. In more particular embodiments, metal ions that may be complexed by the sulfonated iminodialkanoic acids include calcium ions, iron ions, aluminum ions, or any combination thereof. Zinc ions, titanium ions, and/or zirconium ions may also be desirable to complex for similar reasons. By complexing these metal ions and others, it may be possible to preclude their formation of damaging scale or participating in secondary precipitation reactions in a subterranean formation.

In other more particular embodiments, the acid-reactive substance may comprise a siliceous material, which optionally may be present in combination with a carbonate material. When a siliceous material is present, dissolution of the siliceous material may be promoted by hydrofluoric acid or a hydrofluoric acid-generating compound. The hydrofluoric acid or hydrofluoric acid-generating compound may be present in the treatment fluid or introduced to the subterranean formation separately from the sulfonated iminoalkanoic acid. By complexing metal ions that may be present in the subterranean formation, the metal ions may be prevented from undergoing secondary reactions with dissolved silicon compounds or with the hydrofluoric acid itself. For example, by complexing calcium ions, the calcium ions may be prevented from undergoing a secondary reaction to form damaging calcium fluoride precipitates. Accordingly, in some embodiments, the treatment fluids described herein may be used to complex metal ions when dissolving a siliceous material also containing a carbonate material therein. Doing so can allow metal ions from the carbonate material to undergo sequestration so that they do not interfere with the hydrofluoric acid used for dissolution of the siliceous material.

When hydrofluoric acid or a hydrofluoric acid-generating compound is used to promote dissolution of a siliceous material, the hydrofluoric acid or the hydrofluoric acid-generating compound may be present in the treatment fluid comprising the sulfonated iminodialkanoic acid or it may be introduced in a separate treatment fluid. When introduced to the subterranean formation in a separate treatment fluid, the treatment fluid comprising the sulfonated iminodialkanoic acid may be introduced to the subterranean formation first in order to promote metal ion complexation before forming dissolved silicon compounds from the siliceous mineral. Alternatively, the treatment fluid comprising the sulfonated iminodialkanoic acid may pre-condition the subterranean formation before dissolved silicon is formed therein.

As indicated above, when a siliceous material is being dissolved by the treatment fluids of the present disclosure, the treatment fluid can desirably be substantially free of alkali metal ions in various embodiments.

In some embodiments, the treatment fluids described herein may be used in treating a particulate pack in a subterranean formation. Particulate packs may include, for example, proppant packs and gravel packs. Treatment of a particulate pack may beneficially allow the permeability of the pack to be increased, such that it presents a lower impediment to fluid flow.

In some embodiments, the treatment fluids described herein may be utilized in matrix acidizing operations. That is, in some embodiments, the treatment fluids described herein can be introduced to a subterranean formation below a fracture gradient pressure of the subterranean formation. In some embodiments, the interaction of the treatment fluid with the formation matrix may result in the desirable formation of wormholes therein. In other embodiments, the treatment fluids described herein can be introduced to a subterranean formation at or above a fracture gradient pressure of the subterranean formation, such that one or more fractures are created or enhanced in the subterranean formation. Given the benefit of the present disclosure and the understanding of one having ordinary skill in the art, one can readily determine whether to introduce the treatment fluids to a subterranean formation at matrix flow rates (i.e., below the fracture gradient pressure) or at fracturing flow rates (i.e., at or above the fracture gradient pressure).

In some or other embodiments, the treatment fluids described herein may be used in remediation operations within a subterranean formation. Specifically, in some embodiments, treatment fluids described herein comprising a sulfonated iminodialkanoic acid may be used to remove precipitation or accumulation damage within a subterranean formation. As used herein, the term "precipitation or accumulation damage" refers to a siliceous or non-siliceous scale that has been dissolved in a subterranean formation and deposited elsewhere within the subterranean formation.

In some embodiments, the treatment fluids described herein may be used in conjunction with drilling a wellbore penetrating a subterranean formation. For example, when used during drilling, the treatment fluids may desirably leave the subterranean formation conditioned with the chelating agent so that precipitation can be subsequently mitigated at a later time.

In still other various embodiments, systems configured for delivering a treatment fluid of the present disclosure to a downhole location are described herein. In various embodiments, the systems can comprise a pump fluidly coupled to a tubular, the tubular containing a treatment fluid that comprises an aqueous carrier fluid having an acidic pH, a sulfonated iminodialkanoic acid, and ammonium ions. In more particular embodiments, the iminodialkanoic acid can be substantially free of alkali metal ions and have a structure exemplified by Formula 3, in which x is 2, 3, or 4.

The pump may be a high pressure pump in some embodiments. As used herein, the term "high pressure pump" will refer to a pump that is capable of delivering a fluid downhole at a pressure of about 1000 psi or greater. A high pressure pump may be used when it is desired to introduce a treatment fluid of the present disclosure to a subterranean formation at or above a fracture gradient of the subterranean formation, but it may also be used in cases where fracturing is not desired. The treatment fluids described herein may be introduced with a high pressure pump, or they may be introduced following a treatment fluid (e.g., a pad fluid) that was introduced with a high pressure pump. In some embodiments, the high pressure pump may be capable of fluidly conveying particulate matter into the subterranean formation. Suitable high pressure pumps will be known to one having ordinary skill in the art and may include, but are not limited to, floating piston pumps and positive displacement pumps.

In other embodiments, the pump may be a low pressure pump. As used herein, the term "low pressure pump" will refer to a pump that operates at a pressure of about 1000 psi or less. In some embodiments, a low pressure pump may be fluidly coupled to a high pressure pump that is fluidly coupled to the tubular. That is, in such embodiments, the low pressure pump may be configured to convey the treatment fluid to the high pressure pump. In such embodiments, the low pressure pump may "step up" the pressure of a treatment fluid before it reaches the high pressure pump.

In some embodiments, the systems described herein can further comprise a mixing tank that is upstream of the pump and in which the sulfonated iminodialkanoic acid is provided in a concentrate and/or combined with a carrier fluid. Formation of the sulfonated iminodialkanoic acid may also occur in the mixing tank, in some embodiments. In various embodiments, the pump (e.g., a low pressure pump, a high pressure pump, or a combination thereof) may convey the treatment fluid from the mixing tank or other source of the treatment fluid to the tubular. In other embodiments, however, the treatment fluid can be formulated offsite and transported to a worksite, in which case the treatment fluid may be introduced to the tubular via the pump directly from its shipping container (e.g., a truck, a railcar, a barge, or the like) or from a transport pipeline. In either case, the treatment fluid may be drawn into the pump, elevated to an appropriate pressure, and then introduced into the tubular for delivery downhole.

FIG. 1 shows an illustrative schematic of a system that can deliver treatment fluids of the present disclosure to a downhole location, according to one or more embodiments. It should be noted that while FIG. 1 generally depicts a land-based system, it is to be recognized that like systems may be operated in subsea locations as well. As depicted in FIG. 1, system 1 may include mixing tank 10, in which a treatment fluid of the present disclosure may be formulated. The treatment fluid may be conveyed via line 12 to wellhead 14, where the treatment fluid enters tubular 16, tubular 16 extending from wellhead 14 into subterranean formation 18. Tubular 16 may include orifices that allow the treatment fluid to enter into the wellbore. Pump 20 may be configured to raise the pressure of the treatment fluid to a desired degree before its introduction into tubular 16. It is to be recognized that system 1 is merely exemplary in nature and various additional components may be present that have not necessarily been depicted in FIG. 1 in the interest of clarity. Non-limiting additional components that may be present include, but are not limited to, supply hoppers, valves, condensers, adapters, joints, gauges, sensors, compressors, pressure controllers, pressure sensors, flow rate controllers, flow rate sensors, temperature sensors, and the like.

Although not depicted in FIG. 1, the treatment fluid may, in some embodiments, flow back to wellhead 14 and exit subterranean formation 18. Flowback of the treatment fluid may serve to remove complexed metal ions from the subterranean formation, for example. In some embodiments, the treatment fluid that has flowed back to wellhead 14 may subsequently be recovered and recirculated to subterranean formation 18. In other embodiments, the treatment fluid may flow back to wellhead 14 in a produced hydrocarbon fluid from subterranean formation 18.

It is also to be recognized that the disclosed treatment fluids may also directly or indirectly affect the various downhole equipment and tools that may come into contact with the fracturing fluids during operation. Such equipment and tools may include, but are not limited to, wellbore casing, wellbore liner, completion string, insert strings, drill string, coiled tubing, slickline, wireline, drill pipe, drill collars, mud motors, downhole motors and/or pumps, surface-mounted motors and/or pumps, centralizers, turbolizers, scratchers, floats (e.g., shoes, collars, valves, etc.), logging tools and related telemetry equipment, actuators (e.g., electromechanical devices, hydromechanical devices, etc.), sliding sleeves, production sleeves, plugs, screens, filters, flow control devices (e.g., inflow control devices, autonomous inflow control devices, outflow control devices, etc.), couplings (e.g., electro-hydraulic wet connect, dry connect, inductive coupler, etc.), control lines (e.g., electrical, fiber optic, hydraulic, etc.), surveillance lines, drill bits and reamers, sensors or distributed sensors, downhole heat exchangers, valves and corresponding actuation devices, tool seals, packers, cement plugs, bridge plugs, and other wellbore isolation devices, or components, and the like. Any of these components may be included in the systems generally described above and depicted in FIG. 1.

Embodiments disclosed herein include:

A. Methods for synthesizing a sulfonated iminodialkanoic acid. The methods comprise: reacting an iminodialkylnitrile with a sultone under acidic conditions to form a fluid comprising a sulfonated iminodialkanoic acid and ammonium ions.

B. Treatment fluids comprising a sulfonated iminodialkanoic acid. The treatment fluids comprise: an aqueous carrier fluid having an acidic pH; a sulfonated iminodialkanoic acid; and ammonium ions.

C. Systems incorporating a treatment fluid comprising a sulfonated iminodialkanoic acid. The systems comprise: a pump fluidly coupled to a tubular, the tubular containing a treatment fluid comprising an aqueous carrier fluid having an acidic pH, a sulfonated iminodialkanoic acid, and ammonium ions.

D. Methods for treating a subterranean formation. The methods comprise: providing a treatment fluid comprising an aqueous carrier fluid having an acidic pH, a sulfonated iminodialkanoic acid, and ammonium ions; introducing the treatment fluid into a subterranean formation; and complexing one or more metal ions in the subterranean formation with the sulfonated iminodialkanoic acid.

E. Methods for treating a subterranean formation. The methods comprise: providing a treatment fluid comprising an aqueous carrier fluid having an acidic pH, a sulfonated iminodialkanoic acid, and ammonium ions; introducing the treatment fluid into a subterranean formation; at least partially dissolving an acid-reactive substance in the subterranean formation in the presence of the sulfonated iminodialkanoic acid to generate one or more metal ions; and complexing the one or more metal ions in the subterranean formation with the sulfonated iminodialkanoic acid.

Each of embodiments A-E may have one or more of the following additional elements in any combination:

Element 1: wherein the sulfonated iminodialkanoic acid has a structure of

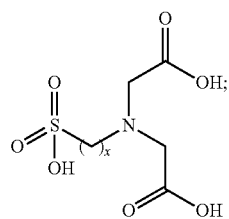

wherein x is an integer ranging between 1 and about 6.

Element 2: wherein x is 2, 3 or 4.

Element 3: wherein the iminodialkylnitrile is iminodiacetonitrile and the sultone is 1,3-propanesultone.

Element 4: wherein the acidic conditions are present in an aqueous solution comprising the iminodialkylnitrile and the sultone, the aqueous solution having a pH of about 2 or less.

Element 5: wherein the iminodialkylnitrile is reacted with the sultone in the aqueous solution at a temperature of about 80° C. or less.

Element 6: wherein the fluid is substantially free of alkali metal ions.

Element 7: wherein the treatment fluid has a pH of about 2 or less.

Element 8: wherein the treatment fluid further comprises hydrofluoric acid or a hydrofluoric acid-generating compound.

Element 9: wherein the treatment fluid is prepared by reacting an iminodialkylnitrile with a sultone under acidic conditions in an aqueous solution to form the sulfonated iminodialkanoic acid.

Element 10: wherein the method further comprises: dissolving an acid-reactive substance in the subterranean formation with the treatment fluid to generate the one or more metal ions.

Element 11: wherein the acid-reactive substance comprises a siliceous material.

Element 12: wherein the acid-reactive substance comprises a carbonate material.

Element 13: wherein providing the treatment fluid comprises: reacting an iminodialkylnitrile with a sultone under acidic conditions in an aqueous solution to form the sulfonated iminodialkanoic acid.

By way of non-limiting example, exemplary combinations applicable to A-E include:

The method of A, the treatment fluid of B, or the system of C in combination with elements 1 and 2; 1 and 4; 3 and 4; 1 and 5; 3 and 5; 1 and 6; 3 and 6; 1 and 7; 3 and 7; 6 and 7; 1 and 8; 3 and 8; 6 and 8; or 7 and 8.

The method of D in combination with elements 1 and 2; 1 and 6; 3 and 6; 1 and 7; 3 and 7; 6 and 7; 1 and 8; 3 and 8; 6 and 8; 7 and 8; 10 and 11; 10 and 12; 8, 10 and 11; 1, 10 and 11; 1, 10 and 12; 3 and 10; 6, 8, 10 and 11; or 7 and 13.

The method of E in combination with elements 1 and 2; 1 and 6; 3 and 6; 1 and 7; 3 and 7; 6 and 7; 1 and 8; 3 and 8; 6 and 8; 7 and 8; 8 and 11; 1 and 11; 1 and 12; 3 and 12; 7 and 10; 7 and 11; 6, 8 and 11; 7 and 13; or 3 and 11.

To facilitate a better understanding of the embodiments of the present disclosure, the following examples of preferred or representative embodiments are given. In no way should the following examples be read to limit, or to define, the scope of the disclosure.

EXAMPLES

Example 1: Synthesis of a Sulfonated Iminodiacetic Acid from Iminodiacetic Acid

The sulfonated iminodiacetic acid was synthesized as generally shown in Reaction 2 above. 15.5 g of iminodiacetic acid (116 mmol) and 14.2 g of 1,2-oxathiolane 2,2-dioxide (116 mmol) were combined in 35 mL water. The reaction mixture was stirred at 85° C. for 4 hours, and reaction progress was monitored by NMR until the resonances of the starting materials disappeared. The resulting aqueous solution was used without purification or further manipulation.

Example 2: Synthesis of a Sulfonated Iminodiacetic Acid from Iminodiacetonitrile A 125 mL roundbottom pressure flask equipped with a magnetic stirrer was charged with 30 mL of water, 11.16 g of iminodiacetonitrile (116 mmol) and 14.2 g of 1,2-oxathiolane 2,2-dioxide (116 mmol). The temperature was raised to 85° C., and the reaction mixture became homogenous after about 5 minutes at that temperature. To the homogenous reaction mixture was then added 58 mmol of sulfuric acid to promote nitrile hydrolysis during the remaining reaction time.

Example 3: Effects of a Sulfonated Iminodiacetic Acid on Calcium Dissolution

Figure 2:
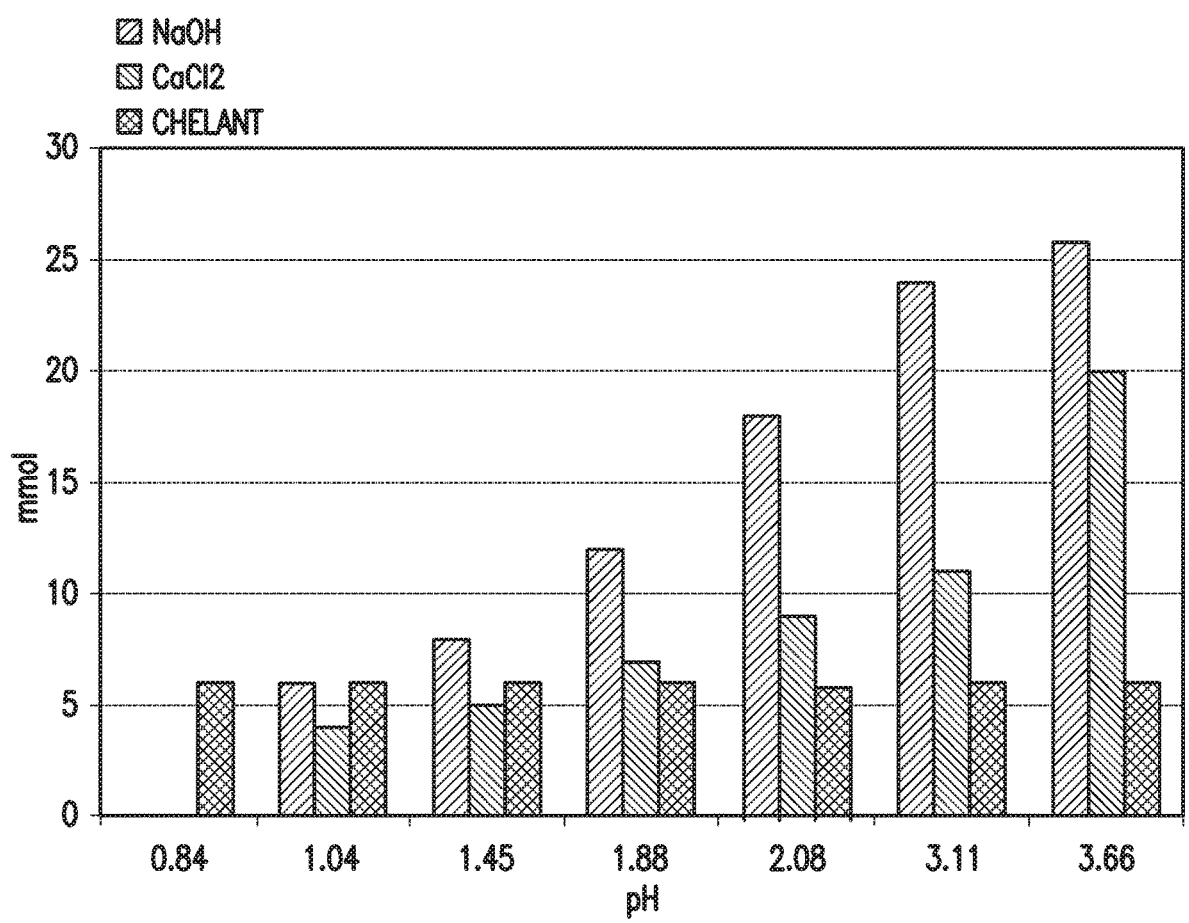
FIG. 2 shows a bar graph summarizing the amounts of $CaCl_2$ and NaOH added to the chelant solution of Example 1 and the resulting pH values.

An aliquot of the reaction mixture from Example 1 was diluted to a volume of 10 mL and a concentration of 0.6 M, and the pH was adjusted to approximately 1. Thereafter, varying amounts of CaCl$_2$ solution and 50% NaOH solution were added to the pH-adjusted aliquot. FIG. 2 shows a bar graph summarizing the amounts of CaCl$_2$ and NaOH added to the chelant solution of Example 1 and the resulting pH values. No precipitate formation occurred in any of the tested configurations, even at pH values and calcium concentrations where calcium hydroxide precipitation would normally be expected to occur.

Example 4: Stabilization of Calcium Ions in the Presence of Hydrofluoric Acid

A control solution was prepared by dissolving CaCl$_2$ and ammonium bifluoride each at a concentration of 0.6 M in 5 mL of water. A test solution was prepared in the same manner as the control solution, except an equivalent molar amount of the chelating agent of Example 1 was added to this solution. The pH value of the control solution was raised to about 7 and the pH value of the test solution was raised to about 4 by adding ammonium hydroxide. Within about 5 minutes, a thick precipitate had formed and settled in the control solution. In contrast, in the test solution, a milky suspension formed, and it did not settle upon standing for 24 hours.

Example 5: Acidizing of a Calcite Core

Figure 3:
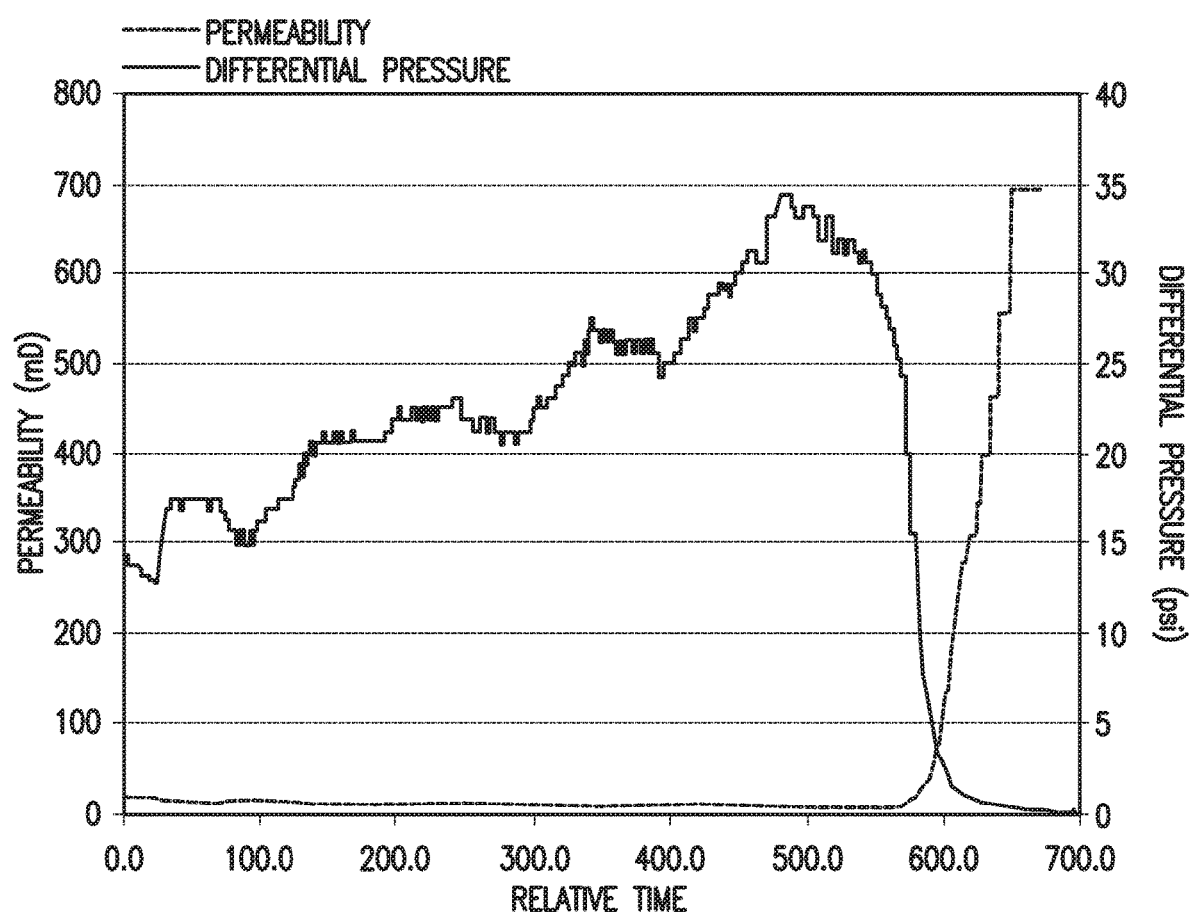
FIG. 3 shows a plot of differential pressure and permeability for a calcite core contacted with the chelant solution of Example 1 as a function of time.

The chelant solution of Example 1 was contacted with a calcite core, and the core's differential pressure and permeability were monitored over time. FIG. 3 shows a plot of differential pressure and permeability for a calcite core contacted with the chelant solution of Example 1 as a function of time. As shown in FIG. 3, a significant drop in differential pressure and an increase in permeability of the core occurred after a contact time period. Thus, it can be concluded that the sulfonated iminodiacetic acid alone was effective to promote dissolution of the calcium carbonate in the core.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
reacting an iminodialkylnitrile with a sultone under acidic conditions to form a fluid comprising a sulfonated iminodialkanoic acid and ammonium ions.

2. The method of claim 1, wherein the sulfonated iminodialkanoic acid has a structure of

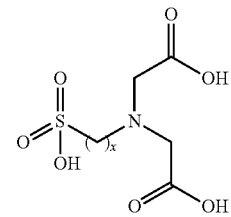

wherein x is an integer ranging between 1 and about 6.

3. The method of claim 1, wherein the iminodialkylnitrile is iminodiacetonitrile and the sultone is 1,3-propanesultone and wherein the acidic conditions are present in an aqueous solution comprising the iminodialkylnitrile and the sultone, the aqueous solution having a pH of about 2 or less.

4. The method of claim 3, wherein the iminodialkylnitrile is reacted with the sultone in the aqueous solution at a temperature of about 80° C. or less.

5. The method of claim 1, wherein the fluid is substantially free of alkali metal ions.

* * * * *